United States Patent
Krajec et al.

[11] Patent Number: 6,047,599
[45] Date of Patent: Apr. 11, 2000

[54] DRAWER STYLE FIXTURE WITH INTEGRAL RF DOOR

[75] Inventors: Russell S. Krajec, Berthoud; Richard J. Chapman, Westminster, both of Colo.

[73] Assignee: Hewlett Packard Company, Palo Alto, Calif.

[21] Appl. No.: 09/026,307

[22] Filed: Feb. 19, 1998

[51] Int. Cl.[7] .......................... G01D 11/24; G01N 23/00; F16M 13/00
[52] U.S. Cl. ..................... 73/431; 250/455.11; 248/636
[58] Field of Search ................... 369/77.1, 77.2; 73/432.1, 431; 248/636; 250/455.11

[56] References Cited

U.S. PATENT DOCUMENTS

| | | | |
|---|---|---|---|
| 5,131,272 | 7/1992 | Minei et al. | 73/431 |
| 5,355,358 | 10/1994 | Van Alfen | 369/77.1 |
| 5,547,635 | 8/1996 | Duthie, Jr. | 250/455.11 |
| 5,609,820 | 3/1997 | Bridges et al. | 250/455.11 |
| 5,691,860 | 11/1997 | Hoppe | 369/77.1 |
| 5,701,216 | 12/1997 | Yamamoto et al. | 369/77.2 |
| 5,787,063 | 7/1998 | Kanno et al. | 369/77.1 |
| 5,867,338 | 2/1999 | Ohira et al. | 369/77.1 |
| 5,901,129 | 5/1999 | Takahashi et al. | 369/77.2 |

*Primary Examiner*—Hezron Williams
*Assistant Examiner*—Chad Soliz

[57] ABSTRACT

The inventive mechanism has an RF door separate from the drawer of an automatic testing machine fixture. The door is either attached to an adapter which holds a device that is to be tested, or attached to a peripheral portion of the fixture. Consequently, changing the adapter is simplified, and the likelihood of damage to the adapter is lowered. When the drawer is in a closed position, the door meshes with the fixture to provide an RF sealed area for RF testing a device.

23 Claims, 2 Drawing Sheets

DRAWER STYLE FIXTURE WITH INTEGRAL RF DOOR

REFERENCE TO RELATED APPLICATIONS

The present application is being concurrently filed with commonly assigned U.S. patent applications, Ser. No. 09/026,065 entitled "QUICKLY REMOVABLE RF SEALED COVER FOR TEST FIXTURE", the disclosure of which is incorporated herein by reference; Ser. No. 09/025,982 entitled "DOCKING STATION FOR AUTOMATED COMMUNICATIONS TEST FIXTURE", the disclosure of which is incorporated herein by reference; Ser. No. 09/026,083 entitled "REMOVABLE FIXTURE ADAPTER WITH RF CONNECTIONS", the disclosure of which is incorporated herein by reference; and Ser. No. 09/026,066 entitled "REMOVABLE FIXTURE ADAPTER WITH PNEUMATIC ACTUATORS", the disclosure of which is incorporated herein by reference.

TECHNICAL FIELD OF THE INVENTION

This application relates in general to automatic testing machines, and in specific to a test fixture for an automatic testing machine which includes a RF door that is connected to the fixture or to an adapter of the fixture.

BACKGROUND OF THE INVENTION

An automatic testing machine (ATM) operates in a production environment to rapidly and accurately test the operation and performance of various types of devices under test (DUT), including RF communication devices. The DUTs could be a finished product or a component of a larger system.

The ATM is programmed to perform various tests on the DUT automatically. For example, RF signals are transmitted to a finished cellular telephone DUT to determine if the telephone activates. Other tests could include environmental tests, such as temperature or vibration tests.

Depending upon the nature and number of the tests being performed, the testing may last from a couple of milliseconds to several minutes. The information from the testing is compared with expected test results. If there is some defect so that the DUT falls below specifications, the ATM will designate the DUT as failed, either by marking the DUT, placing the DUT in a failure area, or indicating the failure to an operator.

The ATM is then loaded with the next DUT, either manually or automatically, and the testing procedure is repeated for this DUT. The information from the testing can be used to evaluate the fabrication process for possible changes, as well as to perform failure analysis on individual failed devices.

Typically, each ATM is designed to perform a specific class of tests on the DUT, and are not able to perform other classes of tests. For example, a vibration ATM may not be able to perform electrical signal tests. However, different types of DUTs may require the same tests to be performed. For example, all types of microcomputer chips are tested for electronic performance characteristics, but different chips will have different locations for power, inputs and outputs. ATMs are made flexible by the use of test fixtures. The test fixture provides an interface between the device under test DUT and the ATM. Thus, a single ATM can perform tests on different types of devices when connected via different fixtures.

However, fixtures tend to be large and bulky. Moreover, they have numerous connections to the ATM for the required resources to allow testing, e.g. power, electronic signals, RF signals, and pneumatic air pressure. Thus changing fixtures is time consuming, as each individual connection to the ATM must be separated, the current fixture removed, and then the new fixture installed. During the replacement process, the production line is shut down, which results in lost production time. If the fixture needs to be repaired, then this process must be undertaken, and the lost production time is unavoidable. However, if the fixture is to be changed merely to accommodate a different DUT, then the lost production time can be mitigated by using an adapter. An adapter is a DUT holder that is coupled to the fixture. The adapter is customized to hold a specific type of DUT. If a different DUT needs to be tested then the adapter in the fixture is swapped for the proper adapter.

A particular class of fixtures are RF fixtures. RF fixtures are used in the testing of DUTs that operate with radio waves, e.g. cellular telephones, pagers, CB radios, etc. The RF fixture is sealed such that external electromagnetic fields or radio waves do not affect the testing of the DUT. Thus, the RF testing being performed on the DUT will be performed accurately, as the DUT will receive only the test RF signals and not any external RF signals which may skew the operation of the DUT. In order to load the DUTs into the fixture, a drawer mechanism is used. A problem arises when adapters are used with RF fixtures having a drawer mechanism.

As shown in FIG. 3, adapter 31 is connected to drawer 34 of fixture 33. RF door 32 is rigidly connected to drawer 34. The arrows 35 indicate the path taken by adapter 31 during its removal from fixture 33. To avoid door 32 and the top of fixture 33, adapter 31 must be lifted vertically to clear door 32, then horizontally to clear the top of fixture 33. Adapters generally are heavy and have fragile connections that are easily damaged. Thus, if adapter 31 collides with either door 32 or the top of fixture 33, then it is likely that adapter 31 will be damaged in some manner.

The damage to adapter 31 may occur without notice by the technician. Thus, when the damaged adapter is subsequently used, then incorrect information about the DUT may be collected. The incorrect information could lead to improperly passing a defective DUT or failing a passing DUT. The incorrect information may also result in incorrect or unnecessary changes being made to the production process. Moreover, the damaged adapter may cause damage to the DUT, the fixture, or the ATM.

Furthermore, since adapter 31 is customized to a particular DUT, multiple copies of the adapter are not usually maintained. Thus, if the adapter is damaged, a backup is not likely to be available. Thus, the production line of the DUT may be halted until the damaged adapter is repaired.

Therefore, there is a need in the art for a system and method that allows for the rapid and reliable replacement of fixture adapters in a production environment.

SUMMARY OF THE INVENTION

These and other objects, features and technical advantages are achieved by a system and method that has the RF door separate from the drawer of the ATM fixture, Since the door is detached from the drawer of the fixture, changing the adapter is simplified and the likelihood of damage to the adapter is lowered. The RF door can be either be fixedly or removably attached to the adapter. The RF door can be attached to a portion of the fixture, such as a peripheral side portion. When the drawer is in a closed position, the door meshes with the fixture to provide an RF sealed area for RF testing a device.

A technical advantage of the present invention is reduction in downtime and errors caused by damaged adapters.

Another technical advantage of the present invention is that the RF door is detached from the drawer mechanism of the fixture.

A further technical advantage of the present invention is that the RF door is attached to the adapter.

A further technical advantage of the present invention is that the RF door is attached to a portion the fixture.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which.

DESCRIPTION OF THE PREFERRED EMBODIMENTS

Figure 1A:
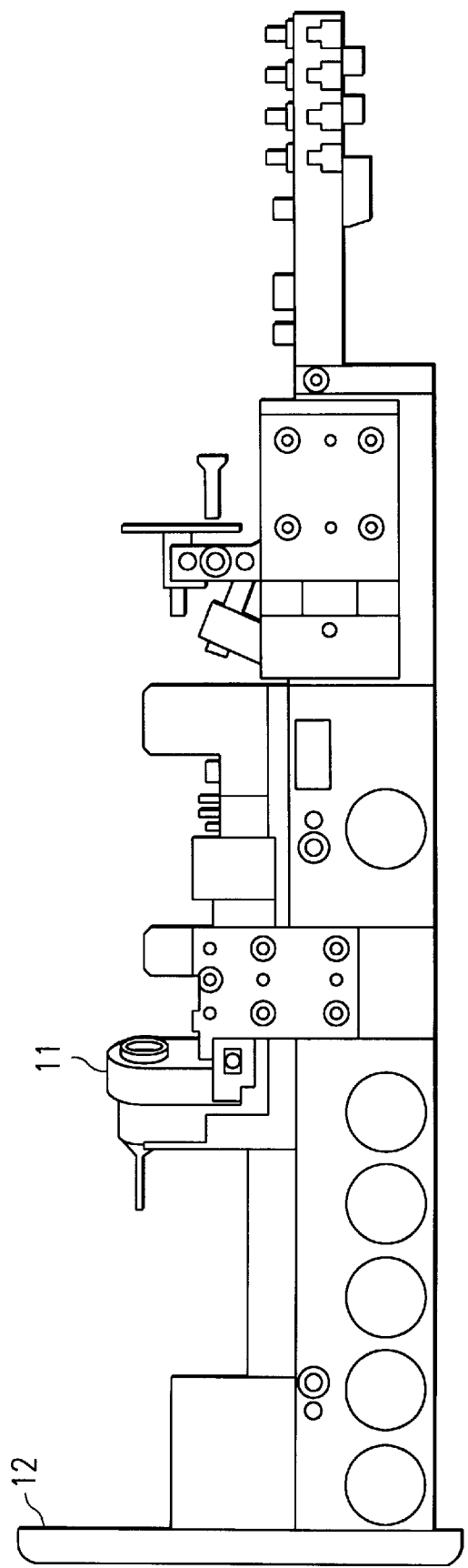
FIGS. 1A and 1B depict the inventive mechanism of an adapter having an attached RF door.
Figure 1B:
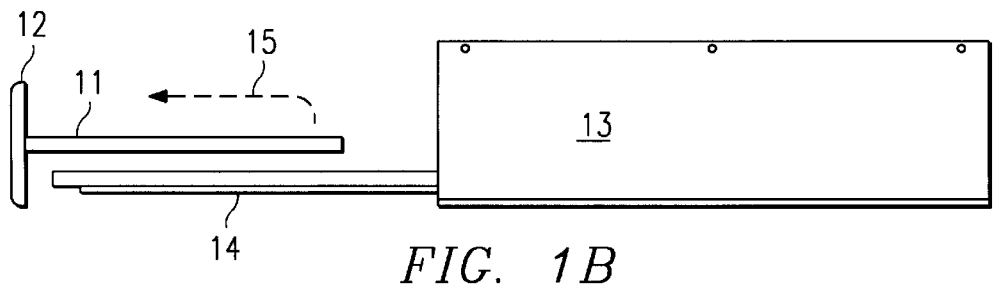

FIG. 1A depicts adapter 11 with an attached RF door 12. FIG. 1B depicts the adapter 11 of FIG. 1A in a partially removed state from the drawer 14. The arrow 15 indicates the path taken by adapter 11 during its removal from fixture 13. Since door 12 is attached to adapter 11, adapter 11 only needs to be lifted slightly to de-couple from a retaining mechanism on drawer 14, such as alignment pins (not shown). Adapter 11 is then moved horizontally. Since little vertical movement is required, adapter 11 is not likely to collide with the top of fixture 13. Since RF door 12 is connected to adapter 11 and is removed from drawer 14 with adapter 11, adapter 11 will not collide with door 12. Therefore, any errors, such as incorrect information or damage to the DUT, fixture, or ATM, which would have arisen from damage to the adapter from collisions with the fixture, are avoided.

RF door 12 is fixedly attached to adapter 11, forming a single, integral piece. Adapter 11 has a rigid mechanical connection, such as pins and/or screws, that takes the load of the drawer sealing. Thus, door 12 will not become dislodged from adapter 11 during repeated cycles of opening and closing during operational use in testing DUTs or otherwise lose RF seal with fixture 13. Moreover, door 12 can optionally include a label, identifying adapter 11 either in terms of the type of DUT for which adapter 11 is specifically customized, or merely identifying the particular adapter. Thus, adapter 11 can be readily identified, even though it is inside fixture 13.

Alternatively, RF door 12 is removably attached to adapter 11. This permits easier storage of adapter 11, as space for door 12 is not needed. Moreover, the number of doors that would have to be maintained would be greatly reduced, as the same few doors could be used for many different adapters. Door 12 could be secured to adapter 11 by using retaining pins or ¼ turn screws. Other securing mechanisms could be used so long as the connection of door 12 to adapter 11 is durable enough to withstand numerous production cycles and maintain a RF seal with fixture 13.

Figure 2A:
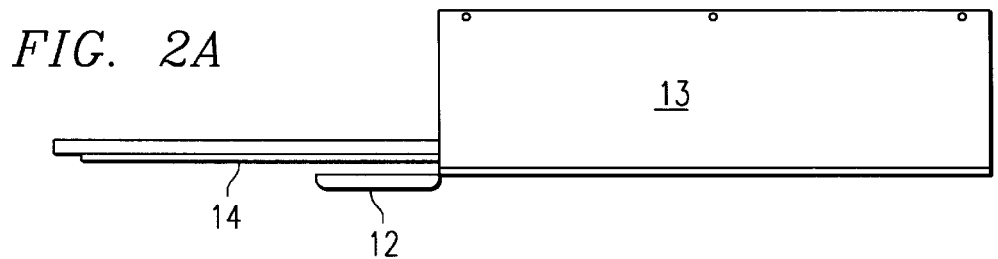
FIGS. 2A, 2B, and 2C depict the inventive mechanism of a peripheral portion of the fixture having an attached RF door.
Figure 2B:
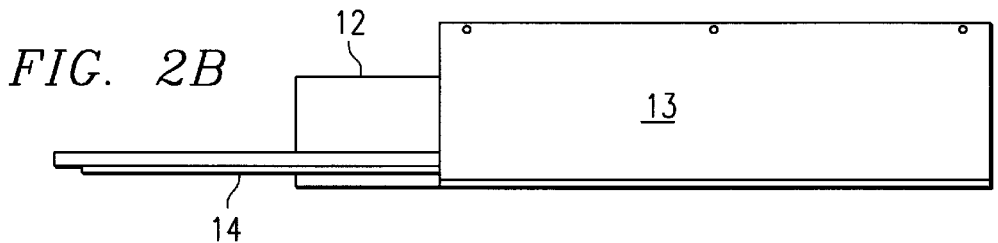
Figure 2C:
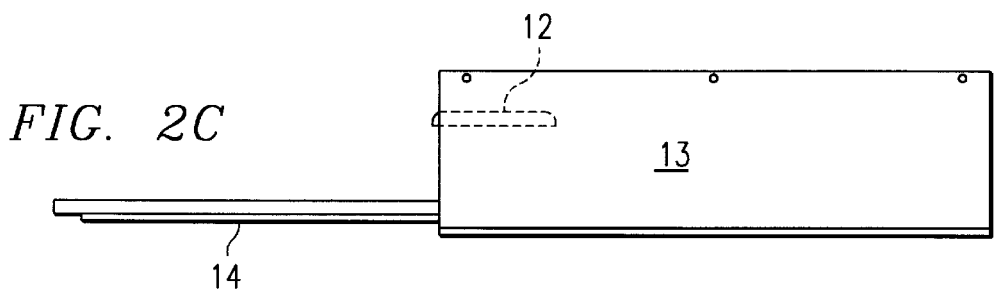
Figure 3:
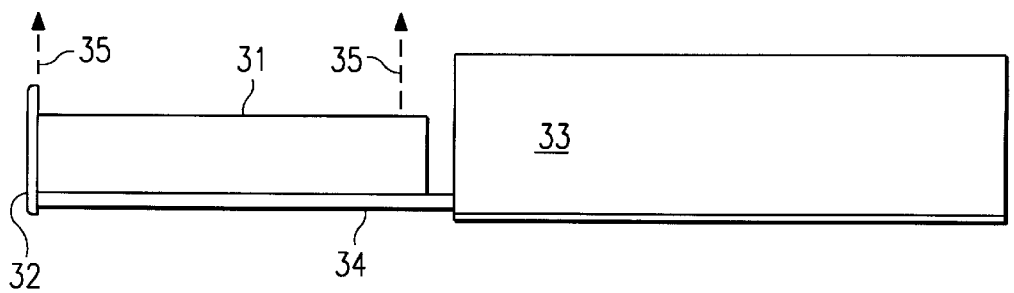
FIG. 3 depicts a prior art arrangement having the RF door attached to the drawer mechanism of the fixture.

Alternatively, FIGS. 2A, 2B and 2C depict different peripheral portions of fixture 13 having an attached RF door 12. FIG. 2A depicts door 12 pivotally attached to the lower peripheral portion of fixture 13. Door 12 could be opened and closed pneumatically by a fixture actuator (not shown). Door 12 could also be opened via a mechanical attachment to drawer 14, such that as drawer 14 moves, door 12 also moves. FIG. 2B depicts door 12 pivotally attached to a side peripheral portion of fixture 13. Note door 12 could be connected to either side of fixture 13, and would operate in a similar manner to the door of FIG. 2A. FIG. 2C depicts door 12 pivotally attached to the upper peripheral portion of fixture 13. Door 12 is shown to open into fixture 13, and thus will not impede the removal of the adapter. However, door 12 could open outward if removal of the adapter is unhindered by the open position of the door, especially if door 12 opens to an approximated vertical position. Door 12 would operate in a similar manner to the door of FIG. 2A. The pivotal connection of FIGS. 2A, 2B, and 2C could be either an internal or external hinge, or pivot pins mounted into peripheral portions of fixture 13 that are adjacent to door 12. Other mechanisms could be used so long as the connection of door 12 to fixture 13 is durable enough to withstand numerous production cycles and maintain a RF seal with fixture 13.

The interior of door 12 and the interior of fixture 13 can optionally be layered with a commercially available RF absorber material. The material typically comprises iron filings in a rubber base. The RF absorber will dampen internal reflections which occur inside the fixture from the test signals and other RF sources located inside the fixture. This prevents any errors from arising during the testing of an RF DUT, which may occur from an echoing of RF energy.

At least one interior surface of door 12 and fixture 13 can optionally be layered with an acoustic absorber material. Such material would be used if the DUT generates or uses noise, for example, a telephone generates a ring, and converts noise to signal and signal to noise. The use of acoustic absorber material would form an anechoic chamber inside the fixture. The material could be foam glued to at least one interior surface of the door and fixture. Alternatively, the absorber could be formed by milling at least one cavity in the door and sides of the fixture. The cavity is then filled with a rubberized adhesive or other sound damping material and sealed with sheet metal, thus forming a sandwich comprising a layer of the fixture (or door) panel, a layer of rubberized adhesive, and a layer of sheet metal. The sheet metal could form the exterior sides of door and fixture, or form the interior sides of the door or fixture. This arrangement is known as a constrained layer dampener. Thus, the DUT will not be improperly influenced by echoing noises, which may cause errors in testing.

Although the present invention and its advantages have been described in detail, it should be understood that various changes, substitutions and alterations can be made herein without departing from the spirit and scope of the invention as defined by the appended claims.

What is claimed is:

1. An adapter for holding a device to be tested that removably couples to a fixture which is attached to an automatic testing machine, wherein the adapter is coupled to the fixture on a drawer mechanism, the adapter comprising:

an attached door;

wherein the device is to be tested with RF, and the attached door mechanically meshes with the fixture when the drawer mechanism is in a closed position to provide an RF seal with the fixture and thereby form an RF sealed area for testing the device.

2. The adapter of claim 1, further comprising:

an interface for attaching the door to the adapter that endures forces involved in closing the door.

3. The adapter of claim 1, wherein:

the door is fixedly attached to the adapter.

4. The adapter of claim 3, further comprising:

identification means affixed to the door for identifying the adapter.

5. The adapter of claim 4, wherein:

the identification means indicates the device for which the adapter is designed to hold.

6. The adapter of claim 1, wherein:

wherein the door is removably attached to the adapter.

7. The adapter of claim 1, wherein:

the door includes means for absorbing interior RF energy.

8. The adapter of claim 1, wherein:

the fixture includes means for absorbing interior RF energy.

9. The adapter of claim 1, wherein:

the door includes means for absorbing interior sound energy.

10. The adapter of claim 1, wherein:

the fixture includes means for absorbing interior sound energy.

11. A fixture that is attached to an automatic testing machine and has a removably coupled adapter for holding a device to be tested, wherein the adapter is coupled to the fixture on a drawer mechanism, the fixture comprising:

an attached door;

wherein the device is to be tested with RF, and the attached door mechanically meshes with the fixture when the drawer mechanism is in a closed position to provide an RF seal with the fixture and thereby form an RF sealed area for testing the device.

12. The fixture of claim 11, wherein:

the door is attached to a lower peripheral portion of the fixture.

13. The fixture of claim 11, wherein:

the door is attached to a side peripheral portion of the fixture.

14. The fixture of claim 11, wherein:

the door is attached to an upper peripheral portion of the fixture.

15. The fixture of claim 14, wherein:

wherein an open position of the door is within the interior of the fixture.

16. The fixture of claim 11, further comprising:

means for opening the door.

17. The fixture of claim 11, wherein:

the door includes means for absorbing interior RF energy.

18. The fixture of claim 11, further comprising:

means for absorbing interior RF energy.

19. The fixture of claim 11, wherein:

the door includes means for absorbing interior sound energy.

20. The fixture of claim 11, further comprising:

the fixture includes means for absorbing interior sound energy.

21. A method for replacing a first adapter that holds a device to be tested with a second adapter, which is removably coupled to a fixture which is attached to an automatic testing machine, wherein the adapter is coupled to the fixture on a drawer mechanism, the method comprising the steps of:

sliding the drawer mechanism to an open position;

removing the first adapter having an attached first door; and installing the second adapter having an attached second door;

wherein the device is to be tested with RF, and the second door mechanically meshes with the fixture when the drawer mechanism is in a closed position to provide an RF seal with the fixture and thereby form an RF sealed area for testing the device.

22. The method of claim 21, wherein the step of removing comprises the steps of:

vertically moving the adapter and door to decouple the adapter from the drawer mechanism; and horizontally moving the adapter away from the fixture.

23. The method of claim 21, wherein the step of installing comprises the steps of:

horizontally moving the adapter toward the fixture and aligning the adapter with the drawer mechanism; and vertically moving the adapter and door to couple the adapter with the drawer mechanism.

* * * * *